US006192103B1

(12) United States Patent
Wormington et al.

(10) Patent No.: US 6,192,103 B1
(45) Date of Patent: Feb. 20, 2001

(54) FITTING OF X-RAY SCATTERING DATA USING EVOLUTIONARY ALGORITHMS

(75) Inventors: Matthew Wormington, Englewood; Charles Panaccione, Littleton; Kevin Monroe Matney, Aurora; David Keith Bowen, Denver, all of CO (US)

(73) Assignee: Bede Scientific, Inc., Englewood, CO (US)

( * ) Notice: Under 35 U.S.C. 154(b), the term of this patent shall be extended for 0 days.

(21) Appl. No.: 09/324,834

(22) Filed: Jun. 3, 1999

(51) Int. Cl.[7] .................................................. G01N 23/207
(52) U.S. Cl. .............................. 378/73; 378/75; 378/76; 378/88
(58) Field of Search .................................. 378/73, 75, 76, 378/86, 88

(56) References Cited

U.S. PATENT DOCUMENTS 4,991,191 * 2/1991 Suryanarayanan ...................... 378/75

OTHER PUBLICATIONS

Csoka, R. et al, "Crystal Structure Determination from Powder Diffraction Data by the Application of a Genetic Algorithm", Materials Science Forum, Trans Tech Publications, Switzerland, vol. 278–281 (1998), pp. 294–299. Aug.
Gale, Julian, "General Utility Lattice Program, Version 1.2", Department of Chemistry, Imperial College, South Kensington, London, pp. 1–82. No Date.
Howell, D.H., "Differential Evolution, An Evolution Stragegy For Genetic Algorithms For Universal Curve And Parameter Fitting And Refinement Applied to Power Diffraction Profiles", pp. 133–134. No Date.
Price, Kenneth V., "Differential Evolution: A Fast and Simple Numerical Optimizer"; pp. 1–4. No Date.
Price, Kenneth et al, "Differential Evolution", Dr. Dobb's Journal, Apr. 1997, pp. 18–24, 78.
Storn, Rainer et al, "Differential Evolution—A simple and efficient adaptive scheme for global optimization over continous spaces", Mar. 1995, pp. 1–12.
Wormington, Matthew, "Theory of Grazing Incidence X-ray Reflectivity and Fluorescence", Denver X-ray Conference Workshop, Aug. 4, 1997.

* cited by examiner

Primary Examiner—David V. Bruce
(74) Attorney, Agent, or Firm—Burns, Doane, Swecker & Mathis, L.L.P.

(57) ABSTRACT

Evolutionary algorithms are used to find a global solution to the fitting of experimental X-ray scattering data to simulated models. A recombination operator combines two or more parameter vectors from one iteration of simulated scattering data to form a new parameter vector for the next iteration, in a manner such that there is a high probability that the new parameter will better fit the experimental data than any of the parent parameters. A mutation operator perturbs the value of a parent vector, to permit new regions of the error function to be examined, and thereby avoid settling on local minima. The natural selection guarantees that the parameter vectors with the best fitness will be propagated into future iterations.

24 Claims, 11 Drawing Sheets

POPULATION, P

| i | $T_1$ | $T_2$ | $R_{sub}$ | $R_1$ | $R_2$ | $D_{sub}$ | $D_1$ | $D_2$ | $E(p)$ |
|---|---|---|---|---|---|---|---|---|---|
| 0 | 250 | 40 | 1 | 1 | 1 | 1 | 1 | 1 | 97 |
| 1 | 149 | 48 | 3 | 6 | 4 | .97 | .93 | 1.03 | 104 |
| 2 | 68 | 12 | 7.9 | 5.2 | 3.1 | .99 | 1.09 | .92 | 44 |
| 3 | 213 | 39 | 5.4 | 6.3 | 7.2 | .93 | 1.01 | .99 | 68 |
| ⋮ | | | | | | | | | |
| m−3 | 197 | 22 | 1.3 | 7.5 | 6.8 | 1.05 | .93 | .92 | 95 |
| m−2 | 296 | 28 | 3.6 | 5.1 | 6.2 | 1.01 | .98 | 1.00 | 31 |
| m−1 | 79 | 47 | 1.4 | 3.2 | 5.8 | 1.02 | .97 | .99 | 59 |

BEST-FIT, b

| $T_1$ | $T_2$ | $R_{sub}$ | $R_1$ | $R_2$ | $D_{sub}$ | $D_1$ | $D_2$ | $E(p)$ |
|---|---|---|---|---|---|---|---|---|
| 296 | 28 | 3.6 | 5.1 | 6.2 | 1.01 | .98 | 1.00 | 31 |

FITTING OF X-RAY SCATTERING DATA USING EVOLUTIONARY ALGORITHMS

FIELD OF THE INVENTION

The present invention relates to X-ray metrology, and more particularly to the fitting of simulation models to X-ray scattering data for the purpose of determining parameters that characterize the structure of a material being tested.

BACKGROUND OF THE INVENTION

In the manufacture of products, it is often necessary to conduct quality assurance measurements at various stages in the manufacturing process, to ensure that the ultimate product meets required specifications. Similarly, during research in the development of new products, it is necessary to be able to quantitatively characterize the structure of a prototype material. These requirements are particularly applicable in the field of advanced materials. In the context of the present invention, the term "advanced materials" encompasses a variety of different types of crystalline, polycrystalline and amorphous materials, including semiconductors, metallic thin films, glasses, coatings, superconductors, and the like. One example of a situation in which these types of measurement are particularly applicable is the manufacture of semiconductor products. Typically, a silicon wafer which forms the starting material for a semiconductor product has an appreciable cost associated with it. Each successive major processing step increases the cost of the overall process by a factor of about ten. Hence, it is necessary to be able to characterize the structure of the wafer during research and throughout the manufacturing process, to identify potential problems and correct them before significant waste occurs. Similar concerns apply in the processing of other types of advanced materials as well.

Originally, destructive testing methods were employed to determine characteristics such as the thickness of various layers of a structure, the roughness of their interfaces, their respective densities, strain and the tilt of crystalline layers. Over time, there has been a tendency to employ larger wafers in the process of manufacturing advanced materials. Because of the cost of each individual wafer, destructive testing methods have become quite uneconomical, and consequently undesirable. For this reason, non-destructive methods are employed.

One particularly useful category of non-destructive testing is X-ray metrology. In addition to being non-destructive, X-ray metrological methods provide several other advantages for both process development and process control of advanced material structures. For instance, they are capable of detecting unacceptable levels of internal defects generated by various processes. Furthermore, as individual material layers on such structures become thinner, traditional methods for measuring thickness and roughness become less accurate, relative to the results that can be achieved by X-rays. A variety of different X-ray metrological methods are known, for measuring different characteristics of a structure. Examples of these methods include X-ray absorption, diffraction, fluorescence, reflectivity, scattering, imaging and fringe analysis. In the context of the present invention, the term "X-ray scattering" is employed as a generic term which collectively encompasses any known X-ray technique that is applied to materials characterization.

The various types of X-ray metrological methods basically involve the projection of an X-ray beam onto a specimen being tested, and measurement of the intensity of the rays which are scattered by the specimen. If the crystallographic structure of a device is known, it is possible to calculate its X-ray scattering. For example, the equations for calculating X-ray diffraction are described by S. Takagi, *Acta Cryst.*, Vol. 15, p. 1311 (1962) and *J. Phys. Soc. Japan*, Vol. 26, p. 1239 (1969), and by D. Taupin, *Bull. Soc. Fr. Mineral Crystallogr.*, Vol. 87, p. 469 (1964). In addition, software programs for modeling and predicting experimental data are commercially available. Examples of such include the RADS program for modeling high resolution X-ray diffraction, and the REFS program for modeling X-ray reflectivity, both of which are distributed by Bede Scientific Instruments Ltd., Durham, UK.

While it is possible to predict the X-ray scattering data that can be obtained from a given structure, the inverse operation cannot be directly achieved. In particular, it is not possible to calculate the structure of a device from its X-ray scattering data. This limitation is due, at least in part, to the fact that the X-ray scattering data only provides a measurement of the intensity of the detected rays, but not their amplitude or phase. As a result, insufficient information is available from which to directly derive the parameters that characterize the structure, such as layer thicknesses, density, surface roughness, strain, etc.

Consequently, to characterize a structure on the basis of its X-ray scattering data, it is necessary to infer such structure by means of a trial-and-error technique. In the known techniques, an iterative procedure is employed, in which a structural model for a specimen is first suggested, on the basis of available information, such as the materials which were employed in the manufacture of the specimen being tested. The X-ray scattering data for this suggested model is then simulated, for example by means of one of the above-mentioned programs, and this simulated data is compared with the experimental, or measured, data from the specimen, either graphically or by using any suitable function which provides an indication of the differences or similarities between them. Based on this information, the suggested model is refined, i.e., certain parameters are changed. The X-ray scattering data for this revised model is then simulated, and compared against the measured data. This process is iteratively repeated until the difference between the simulation and the actual data converges to a minimum or falls below a predefined threshold.

This iterative procedure can be characterized as a non-linear data fitting problem. Given a particular curve, i.e., the experimental data, it is necessary to find a known curve which most closely matches the experimental curve. The parameters which define the known curve are then assumed to be those which characterize the tested specimen. In the past, various approaches have been applied to non-linear data fitting. In one approach, known as direct search, the parameter space is divided into small, but finite, regions. An error function is calculated for each region, and the region that produces the smallest error value is chosen as the best-fit parameter vector. In a related approach, known as the Monte Carlo method, the parameter space is again divided into small regions. The regions are selected at random, and the error function is evaluated for each. After a certain number of regions have been chosen, or when the error value is smaller than a specified value, the search is stopped. The region with the smallest error value is chosen as the best fit.

Other approaches to parameter optimization are also well known. In one approach, identified as Downhill Simplex, an initial guess for the best-fit parameters is made by the user. A geometrical construct known as a simplex then moves in directions that decrease the error value. The parameter vector that yields the smallest error value in the neighborhood of the initial guess is chosen as the best-fit parameter vector. In the Levenberg-Marquardt method, an initial guess for the best-fit parameters is again made by the user. This method combines linearization and gradient searching of the error function, to minimize the error in the neighborhood of the initial guess. The parameter vector which provides the smallest error value is selected as the best fit.

These latter methods have relatively limited usefulness, since they are highly dependent upon the accuracy of the initial estimate. In operation, they tend to settle upon a local minimum in the error function which is in the neighborhood of the initial estimate. An optimal solution, i.e., a global minimum, which is significantly different from the initial guess may never be found, because of the manner in which they operate. Hence, the fitting can only be carried out by a person having a high level of skill who is able to make an accurate initial estimate. Even then, it may take several hours to find the best solution.

To avoid the problem of having to start with an estimate that is close to the optimum solution, another approach known as simulated annealing has been employed. This approach uses the physical principles that govern annealing, namely the slow cooling of a liquid so that it forms a crystal, to obtain the best-fit parameters. While this approach provides improved results, in that it is capable of escaping from local minima, it can be quite difficult to design and set up the annealing schedule. The process also requires a considerable amount of time, since it does not search the parameter space in an efficient manner, and therefore is not well suited for on-line quality control for processes.

It is desirable, therefore, to provide a technique for fitting experimental X-ray scattering data to simulated data which operates in an efficient and robust manner to find a global solution, while avoiding the need to begin with an estimate that is close to the optimum, and which can therefore be practiced by non-skilled operators.

SUMMARY OF THE INVENTION

In accordance with the present invention, the foregoing objectives are achieved by the use of genetic algorithms, particularly evolutionary algorithms, to fit experimental X-ray scattering data to simulated models. In general, evolutionary algorithms can be characterized as optimization (or minimization) methods that are based on concepts of genetics and natural selection. Through genetic operators and natural selection, parameter vectors that provide small error values are located. A particular evolutionary algorithm known as Differential Evolution employs a recombination operator that combines two parameter vectors from one generation of vectors to form a new parameter vector for the next generation, in a manner such that there is a high probability that the new parameter will better fit the experimental data than either parent parameter. A mutation operator perturbs the value of the new parameter vectors, to permit new regions of the error function to be examined. The natural selection guarantees that the parameter vectors with the best fitness will be propagated into future generations.

Among the advantages offered by the use of evolutionary algorithms to fit X-ray scattering data is the fact that they optimize the tradeoff between exploring new points in the parameter space, via mutation, and exploiting the information which has already been developed, via recombination. In addition, evolutionary algorithms operate on several solutions simultaneously, to provide implicit parallelism, by gathering information from current search points to direct the search. This approach is equivalent to an extensive search of the parameter space without directly testing all values. The ability to maintain multiple solutions concurrently reduces the susceptibility of evolutionary algorithms to problems associated with local minima and noise. Consequently, the evolutionary algorithm is capable of identifying a global solution even when the starting values differ from the true values by a factor of two or more.

The X-ray scattering data fitting technique of the present invention requires virtually no user intervention once it is initiated, and thereby reduces the time that it takes to model a structure from experimental data. In addition, since it is not highly dependent upon the skill of an operator, it improves the quality and repeatability of the match, and thereby provides information that enables better materials to be made. Furthermore, the results of the fitting provide quantitative information about the material that can be used in material specifications.

The foregoing features of the invention, and the advantages achieved thereby, are explained in greater detail hereinafter with reference to particular embodiments illustrated in the accompanying drawings.

DETAILED DESCRIPTION

To facilitate an understanding of the principles which underlie the present invention, it will be described hereinafter with particular reference to its implementation in connection with specular X-ray reflectivity data. It will be appreciated, however, that the practical applications of the invention are not limited to this particular embodiment. Rather, the invention will find utility in a variety of different X-ray metrological methods where it is desirable to fit measured, or experimental, data to a simulated model to determine characterizing parameters of a structure.

Figure 1:
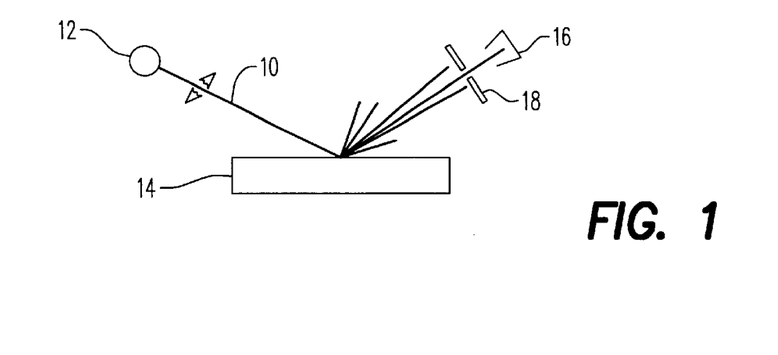
FIG. 1 is a schematic illustration of one type of X-ray measurement technique in which the present invention can be employed.

A general overview of a system for providing X-ray reflectivity data is illustrated in FIG. 1. Referring thereto, a beam of X-rays 10 is directed from a suitable source 12 to the surface of a specimen 14 whose characteristics are being measured. The intensity of the X-rays which reflect off the specimen are measured in a detector 16. The detector is located behind a suitable aperture 18, which ensures that the detected X-rays are those which reflect off the specimen at a predefined angle. During the testing, the incident beam 10 is scanned over a predetermined range of angles, and the intensity of the reflected and scattered X-rays is detected over this range. The scanning can be carried out by moving the source 12, or by rotating the specimen 14 relative to the source.

Figure 2:
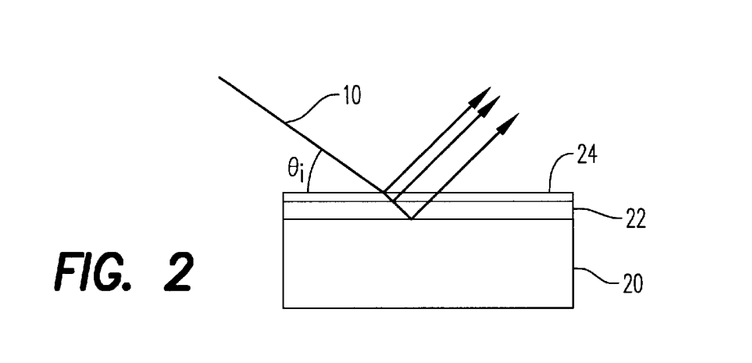
FIG. 2 is a more detailed illustration of the interaction between the incident X-ray beam and the layers of a specimen.
Figure 3:
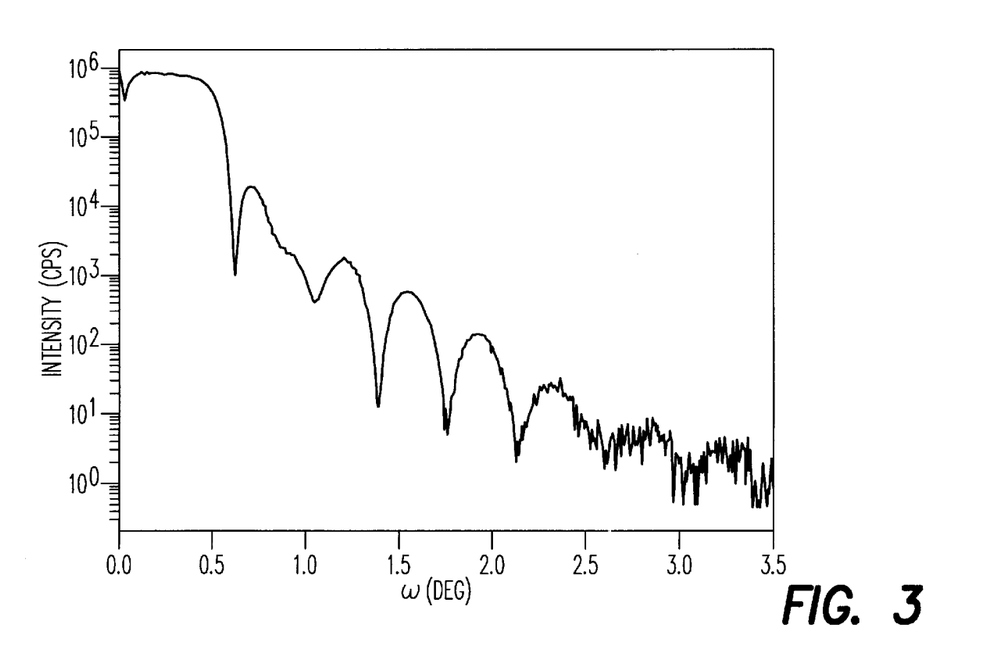
FIG. 3 is a graph of the measured intensity over a range of incidence angles for a specimen.

FIG. 2 provides a more detailed illustration of the structure of the specimen, and its effects upon the incident X-rays. The example of FIG. 2 illustrates a specimen consisting of a substrate 20 of $Al_2O_3$ with an intermediate layer 22 of Ta deposited on it, and a film 24 of $Ta_2O_5$ formed on top. Depending upon the angle of incidence $\theta_i$, some portion of the incident X-rays from the beam 10 will be reflected off the surface of the topmost film 24. The remainder of the beam penetrates the film, and a portion of this is reflected at the interface of the Ta layer 22 and the uppermost film 24, and emerges from the surface of the specimen. Another portion of the penetrating rays travel through the intermediate layer 22, and are reflected at its interface with the $Al_2O_3$ substrate 20, and again emerge from the surface of the specimen. These X-rays which are reflected at the various surfaces of the specimen interfere with one another, to produce a fringe pattern, which is measured by scanning the specimen and detector over a predetermined range. An example of the detected data is illustrated in FIG. 3. The abscissa of the illustrated graph indicates the angle over which the incident beam is scanned, in arcseconds, and the ordinate axis identifies the log of the measured intensity. As can be seen, at a low angle of incidence less than about 0.5°, the measured intensity is quite high, indicating almost total reflection. As the angle of incidence increases, a greater proportion of the beam penetrates into the structure of the specimen, resulting in the interference patterns as well as a decrease in the reflected intensity.

The particular interference pattern that results from the X-ray reflectivity is influenced by a number of factors. These factors include the composition of the material that forms each of the respective layers, the thicknesses of the layers, the roughness of the surface and the interfaces between layers, and the density of the material within the layers. In essence, the values for these factors form parameters that can be used to characterize the specimen.

Figure 4:
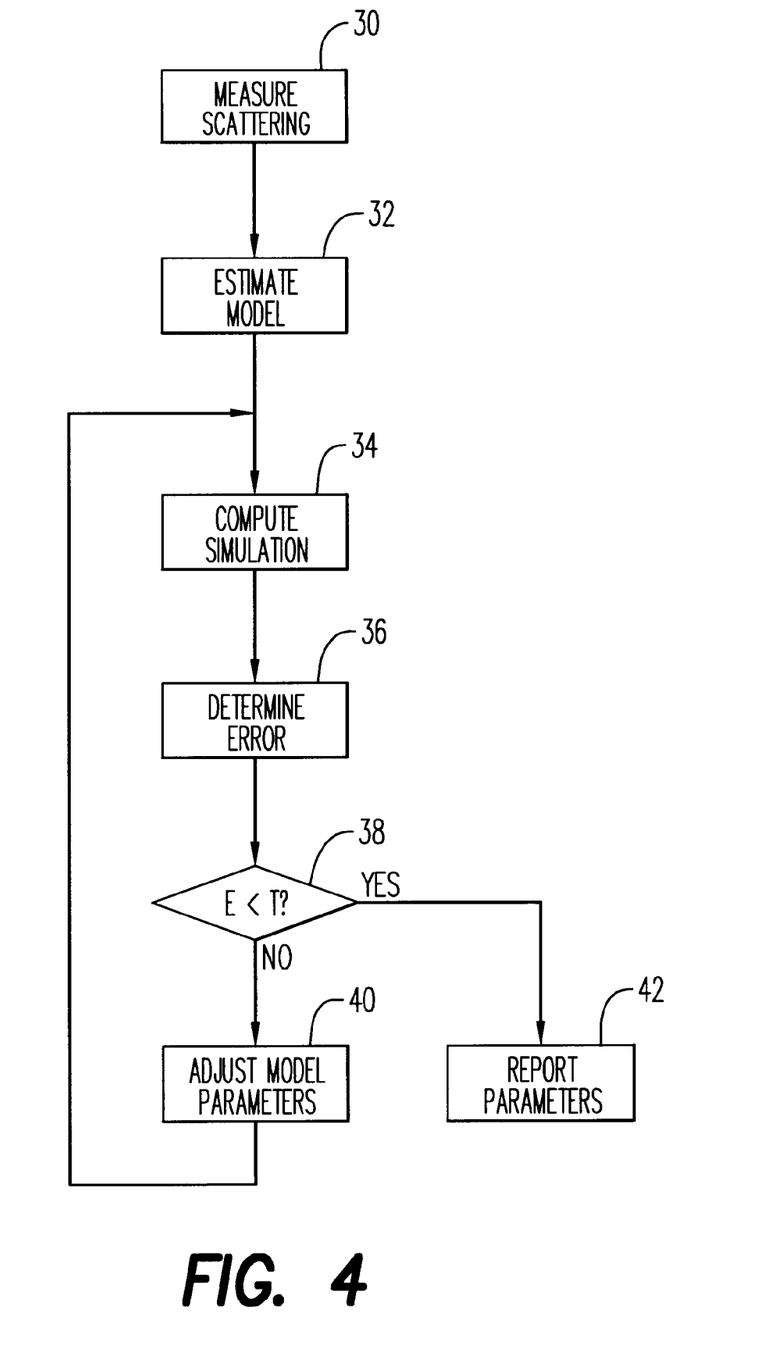
FIG. 4 is a flowchart of the general procedure for deriving the best fitting simulation model for a given set of experimental data.

If the structure of a specimen is known, it is possible to calculate the X-ray scattering data for that specimen, using known principles. In other words, for any given structure, the curve which identifies its characteristic interference fringe pattern can be simulated. See, for example, Bowen et al, "Principles and Performance of a PC-based Program for Simulation of Double-axis X-ray Rocking Curves of Thin Epitaxial Films", *Mat. Res. Soc. Symp. Proc.* 208, pp. 113–118, 1991; and Wormington et al, "Principles and Performance of a PC-based Program for Simulation of Grazing Incidence X-Ray Reflectivity Profiles", *Mat. Res. Soc. Symp. Proc.* 238, pp. 119–124, 1992. Conversely, however, it is not possible to directly derive the structure of a specimen from its interference fringe pattern, for reasons discussed previously, except in extremely simple cases. Thus, it is necessary to infer the structure of the specimen by simulating the data for known models, and determining which set of data best fits the experimental data obtained from the specimen being tested. This result is accomplished by means of an iterative, trial-and-error process which is generally illustrated in the flowchart of FIG. 4.

Referring to the figure, the fitting procedure begins by measuring the X-ray scattering data for a specimen being tested, at step 30. A model for that specimen is then estimated at step 32, based upon all available information. For instance, if the operator is familiar with the process by which the specimen was created, information such as the composition of the individual layers in the specimen and their nominal thicknesses should be available. For those parameters which are unknown, such as surface roughness and/or layer density, operators can use their best guess. Once the model has been estimated, the X-ray scattering for that model is simulated at step 34, using known methods such as those described in the aforementioned references, to produce a characteristic curve. The differences between the values for that curve and the data which was measured at step 30 are determined at step 36, using a suitable function which generates an error value. Preferably, the error function generates small values when there is close agreement between the measured data and the simulated data. At step 38, a determination is made whether the error value is less than a threshold value T. If it is not, one or more parameters of the model are adjusted at step 40. During this adjustment, the operator attempts to minimize the error value. It can be seen, therefore, that as the number of parameters increases, the minimization problem becomes significantly more complex. In particular, it increases as the power of the number of parameters. After the model parameters have been adjusted, steps 34, 36 and 38 are repeated. The operator continues to adjust the model, until the error value falls below the threshold, or a maximum number of iterations have been performed. At this point, the parameters of the model are reported out, at step 42, as the best fit for the measured data.

Figure 5A:
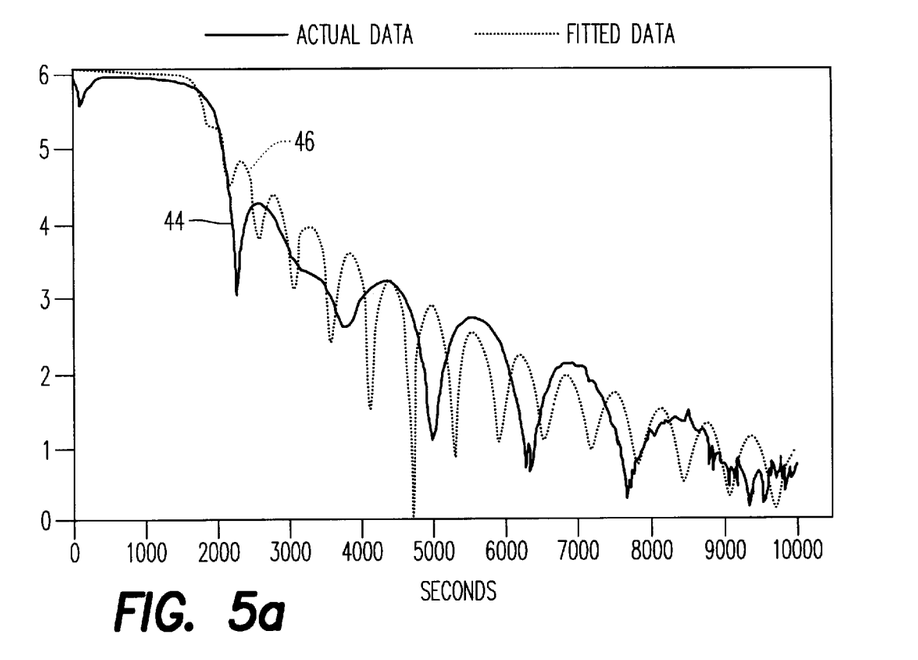
FIGS. 5a–5d are graphs illustrating representative stages in the data fitting process.
Figure 5B:
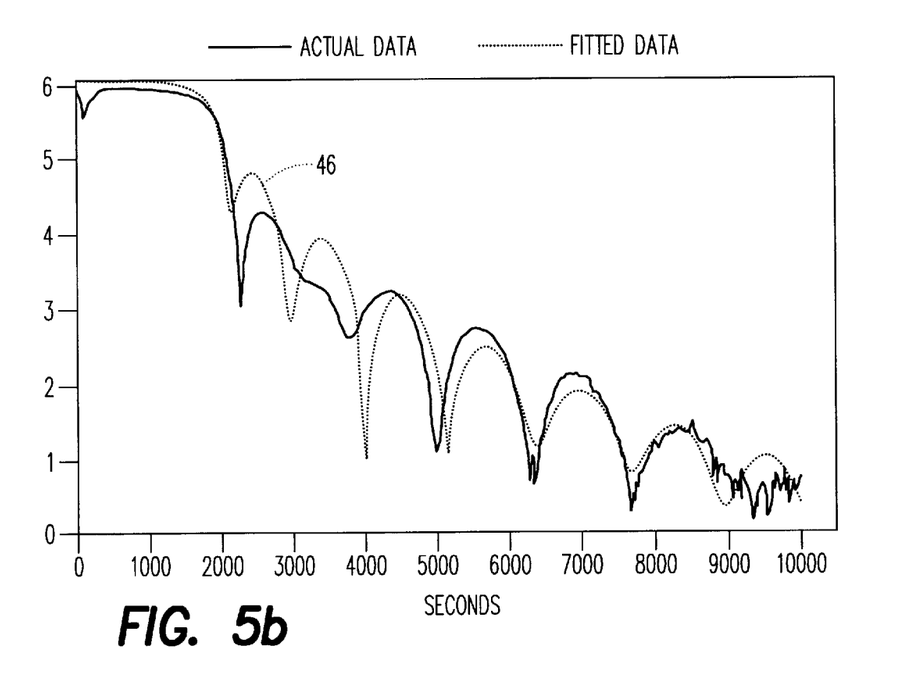
Figure 5C:
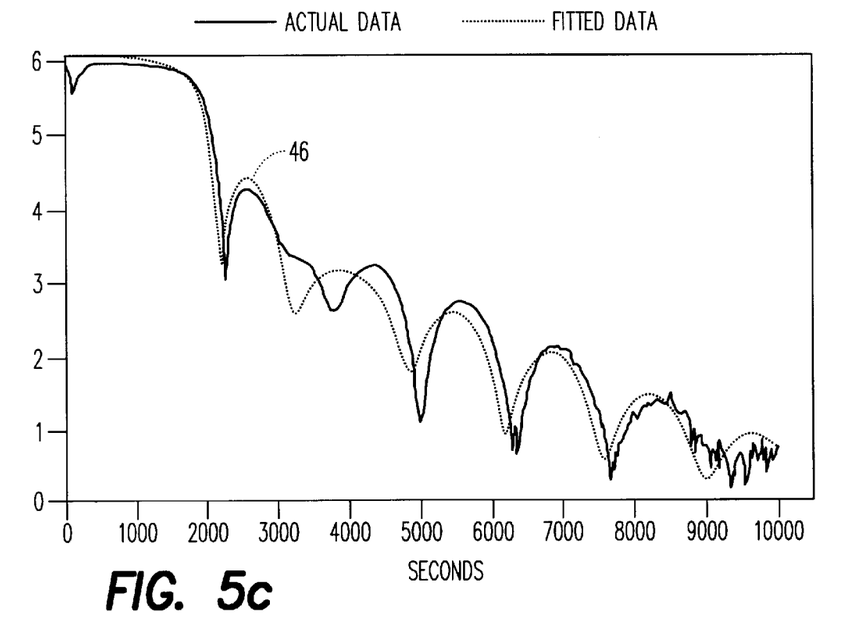
Figure 5D:
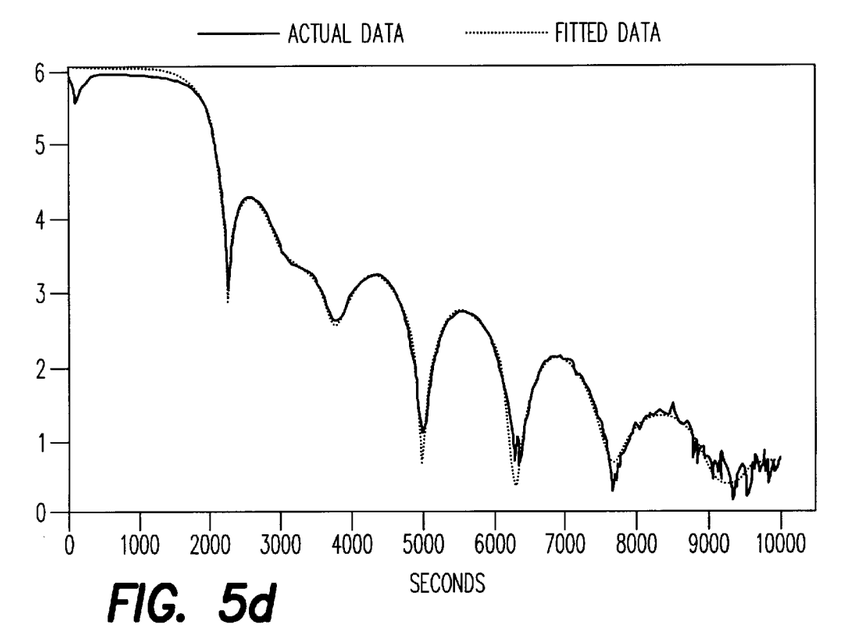

FIGS. 5a–5d illustrate the results that might be obtained at various stages in the process. FIG. 5a depicts a curve 44 representative of measured data, and a curve 46 which is simulated from an estimated model. As can be seen, the two curves are significantly different from one another. FIGS. 5b and 5c illustrate that the curve 46 for the estimated model begins to approach that for the measured data as the model parameters are adjusted. Finally, at FIG. 5d, the best fitting model for the measured data has been obtained. As can be seen, the curve for the model closely matches the measured data at lower angles of incidence. At the higher angles of incidence, the noise in the measured data becomes more significant, resulting in the differences between the measured data and the best-fit curve. It should be noted that, although FIGS. 5a–5d only depict four representative graphs, several hundred and possibly even thousands of iterations of the procedure represented in FIG. 4 may be required to go from the initial estimate of FIG. 5a to the best-fit curve of FIG. 5d, in dependence upon the approach that is employed to derive the final result.

The use of an appropriate error function at step 36 can be an important factor in the data-fitting method, regardless of the minimization approach that is used. Ideally, the error function should have the following properties:

the function should be continuous and single-valued in the parameter space;

the function should have a deep global minimum;

local minima should be much less deep than the global minimum;

the function should be rapidly calculable;

the function should not be very sensitive to the absolute magnitude of the data, since X-ray scattering data is often collected over many orders of magnitude; and the function should not over-emphasize outlying points in the difference between the simulated and experimental data, since a Poisson distribution of statistical noise can be expected in the data set.

A number of functions that have commonly been used in optimization problems could be employed, such as:

1. Mean-squared error of the data (MSE)

$$E(p) = \frac{1}{N-1}\sum_{j=1}^{N}[I_j - I(\theta_{j,p})]^2$$

2. Mean-squared error of the log-transformed data ($MSE_{log}$)

$$E(p) = \frac{1}{N-1}\sum_{j=1}^{N}[\log I_j - \log I(\theta_{j,p})]^2$$

3. Mean-absolute error of the data (MAE)

$$E(p) = \frac{1}{N-1}\sum_{j=1}^{N}|I_j - I(\theta_{j,p})|$$

4. Mean-absolute error of the log-transformed data ($MAE_{log}$)

$$E(p) = \frac{1}{N-1}\sum_{j=1}^{N}|\log I_j - \log I(\theta_{j,p})|,$$

where $I_j$ represents the measured intensity of the specimen at an incidence angle $\theta_j$, N is the total number of measured points ($\theta_j$, $I_j$) during a scan, j=1,2, . . . ,N, and $I(\theta_j,p)$ is the simulated data that is computed for the incidence angle $\theta$; using a structural model with n adjustable parameters represented by the vector p=[$p_1,P_2, \ldots ,P_n$].

Tests of these functions against actual X-ray scattering data show that the non-logarithmic functions (1) and (3) do not effectively fit the data at low intensities. These lower intensity values occur at high scattering angles, and contain information on the smallest layer spacings in the material, which are often those of most interest. In the case of high-resolution X-ray diffraction, structures such as high electron mobility transistors (HEMTs) or heterojunction bipolar transistors (HBTs) produce characteristic curves in which the significant information is four or more orders of magnitude below the substrate peak height. Both error functions (2) and (4) cope adequately with such data, and function (4) is preferred because of its lower sensitivity to outliers. In addition, the error function has greater immunity to noise than an approach which employs squares of differences, or the like, because the terms are linear rather than quadratic.

However, a non-logarithmic function may be more appropriate for other types of data, such as powder diffraction, or X-ray interferometric fringes, where the most significant information is contained in the higher intensities and there is a smaller intrinsic dynamic range. In such cases the MAE function (3), or some other robust function that is less sensitive to outlying points than a least squares function, may be more preferable.

In accordance with the present invention, the adjustment of the model parameters at step 40, to obtain the best fit, is carried out with the use of genetic algorithms, and preferably a class of genetic algorithms knows as evolutionary algorithms. Basically, evolutionary algorithms are iterative procedures which employ the principle of "survival of the fittest" in determining successive generations of data. Guided by an error function E(p), the evolutionary algorithm attempts to optimize a parameter vector p by a repeated cycle of mutation, recombination and selection. At the outset of the data fitting procedure, an initial population of representative data is generated. In the context of X-ray scattering, therefore, the initial population comprises various sets of the parameters that are used to characterize a specimen. Each of the members of the population is then evaluated, according to a suitable error function, such as the $MAE_{log}$ function, to determine its associated error value. Randomly selected members of the population are combined with one another, according to any suitable function, to produce a candidate for a subsequent generation of the population. In a further aspect of the algorithm, the candidate member can be mutated, i.e., its value is changed, in either a random fashion or according to a predetermined function, to more fully search the parameter space. After a candidate member has been produced in this manner, it is evaluated for possible inclusion in a new generation. The error value for the candidate member is compared against that of a member of the prior generation, and the member having the lower error value survives for the next generation.

The process continues until a predetermined number of iterations have been performed, or a set period of time has elapsed. At this time, the member of the surviving generation having the lowest error value is chosen as the best fit.

The use of evolutionary algorithms to determine the best model for the measured data, as well as the simulation of X-ray scattering data, can be carried out in a suitably programmed general purpose computer. The application of an evolutionary algorithm to a relatively simple example of X-ray scattering data is generally illustrated in the flow chart of FIG. 6, with reference to the exemplary specimen depicted in FIG. 2. The characterizing information for this specimen, to be determined by the X-ray reflectivity measurement, comprises the thickness of the Ta layer 22, the thickness of the $Ta_2O_5$ film 24, the roughness of the interface between the substrate 20 and the Ta layer 22, the roughness of the interface between the Ta layer 22 and the $Ta_2O_5$ film 24, the roughness of the external surface of the $Ta_2O_5$ film 24, and the densities of each of the substrate 20, the Ta layer 22 and the $Ta_2O_5$ film 24. Hence, there are a total of eight parameters that are used to characterize the structure of the specimen. In essence, every set of values for these eight parameters can be viewed as a vector in an 8-dimensional parameter space.

Figure 6:
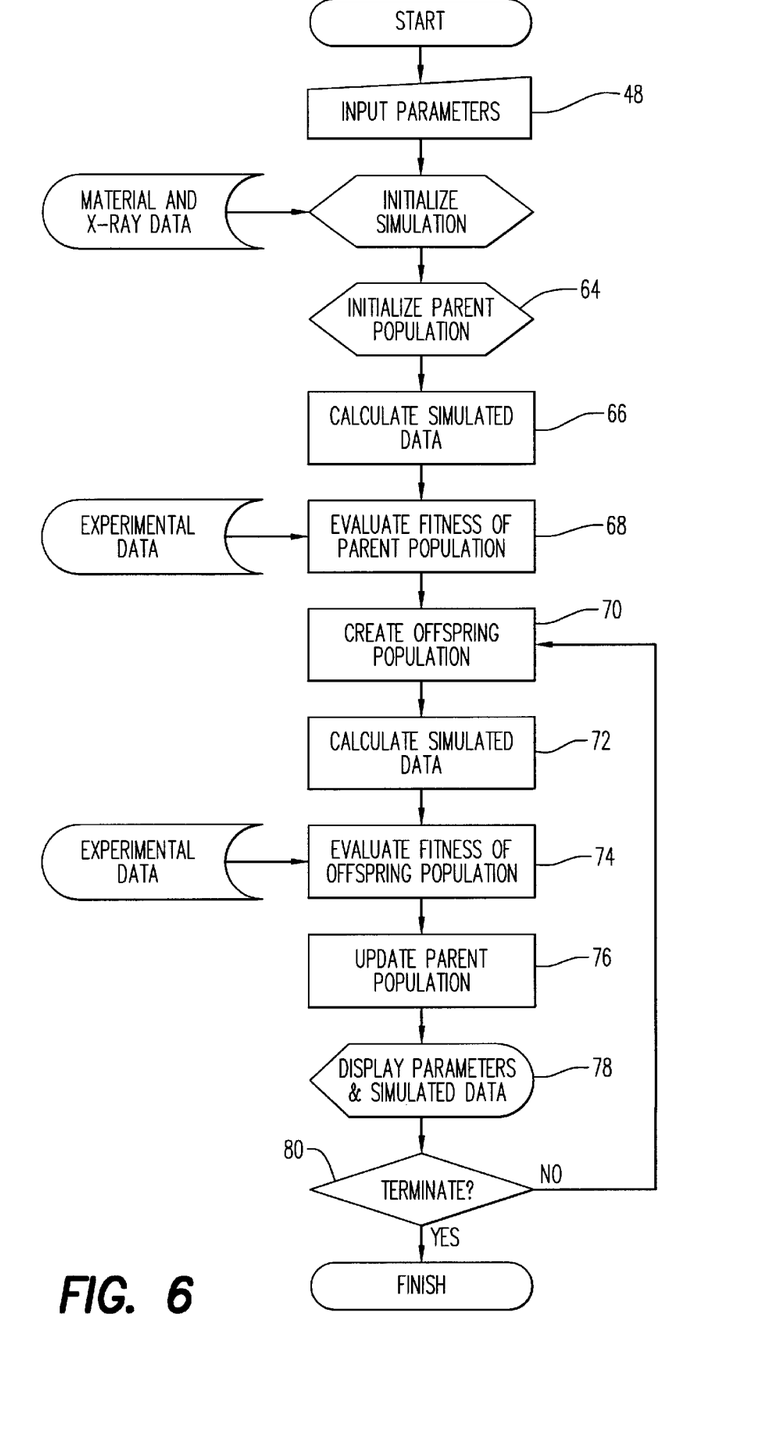
FIG. 6 is a flowchart illustrating the general application of evolutionary algorithms to X-ray scattering data in accordance with the present invention.
Figure 7:
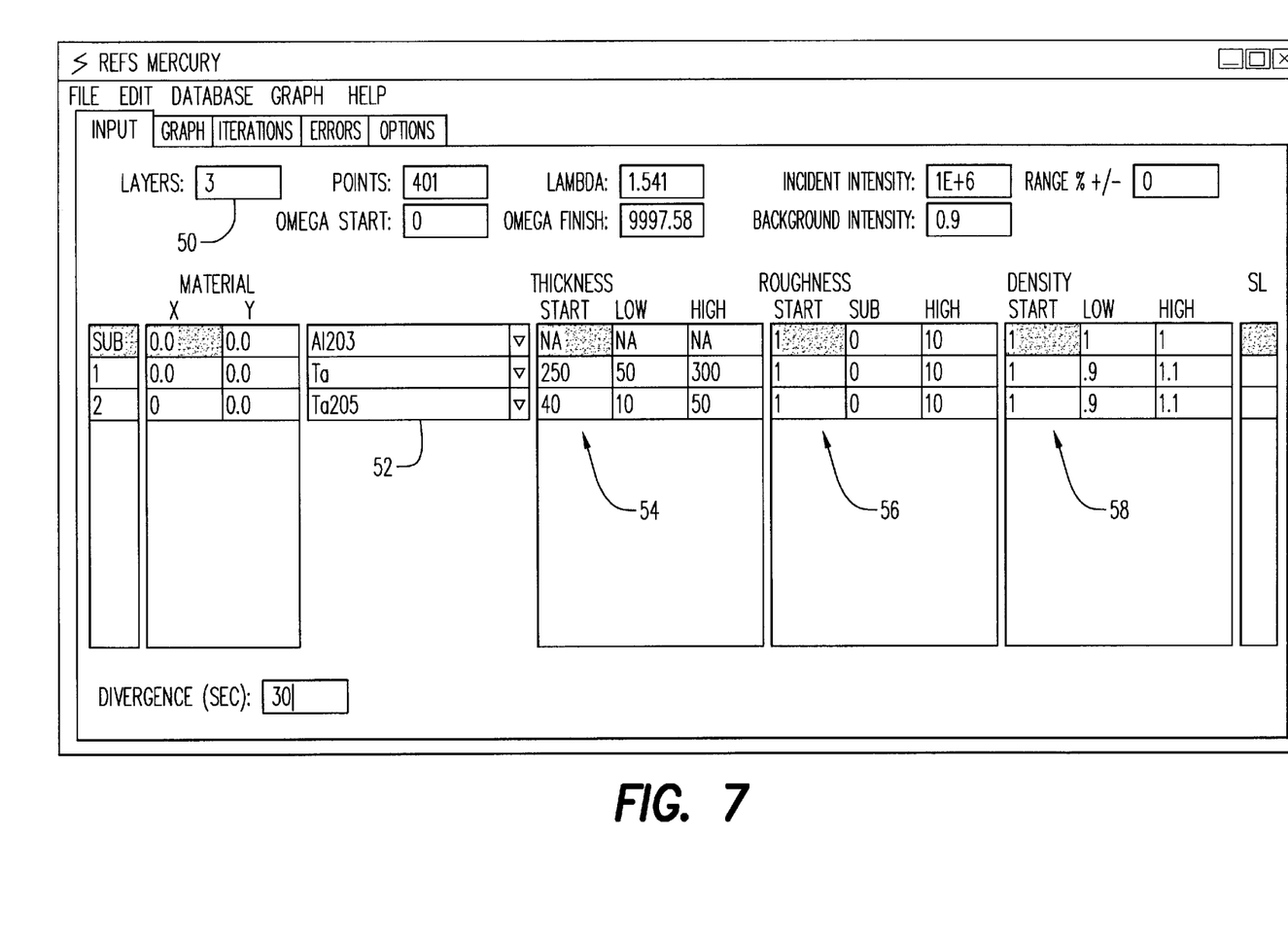
FIG. 7 is an illustration of a user input interface window.

Referring to FIG. 6, at step 48 the operator enters an initial value for each of the eight parameters of interest, as an estimate of the specimen's structure. FIG. 7 illustrates an exemplary type of graphical user interface that can be employed for this input function. In a window 50, the user can enter the number of layers in the specimen. In response to this entry, three additional windows 52 appear, in which the user can enter the material for each of the substrate and the first and second layers. Initial values for the thickness, roughness and density parameters for each of these layers are entered in columns 54, 56, and 58, respectively. Associated with each of these data entry columns are additional columns in which the operator can specify the high and low limits for each of the parameters, to thereby constrain the range of values over which the data fitting process is carried out. If the low and high limit values of any parameter are set equal to the starting parameter value, that parameter remains fixed throughout the fitting procedure. The interface might also permit the user to specify the maximum length of time or maximum number of iterations over which the fitting procedure is to be carried out.

Figure 8:
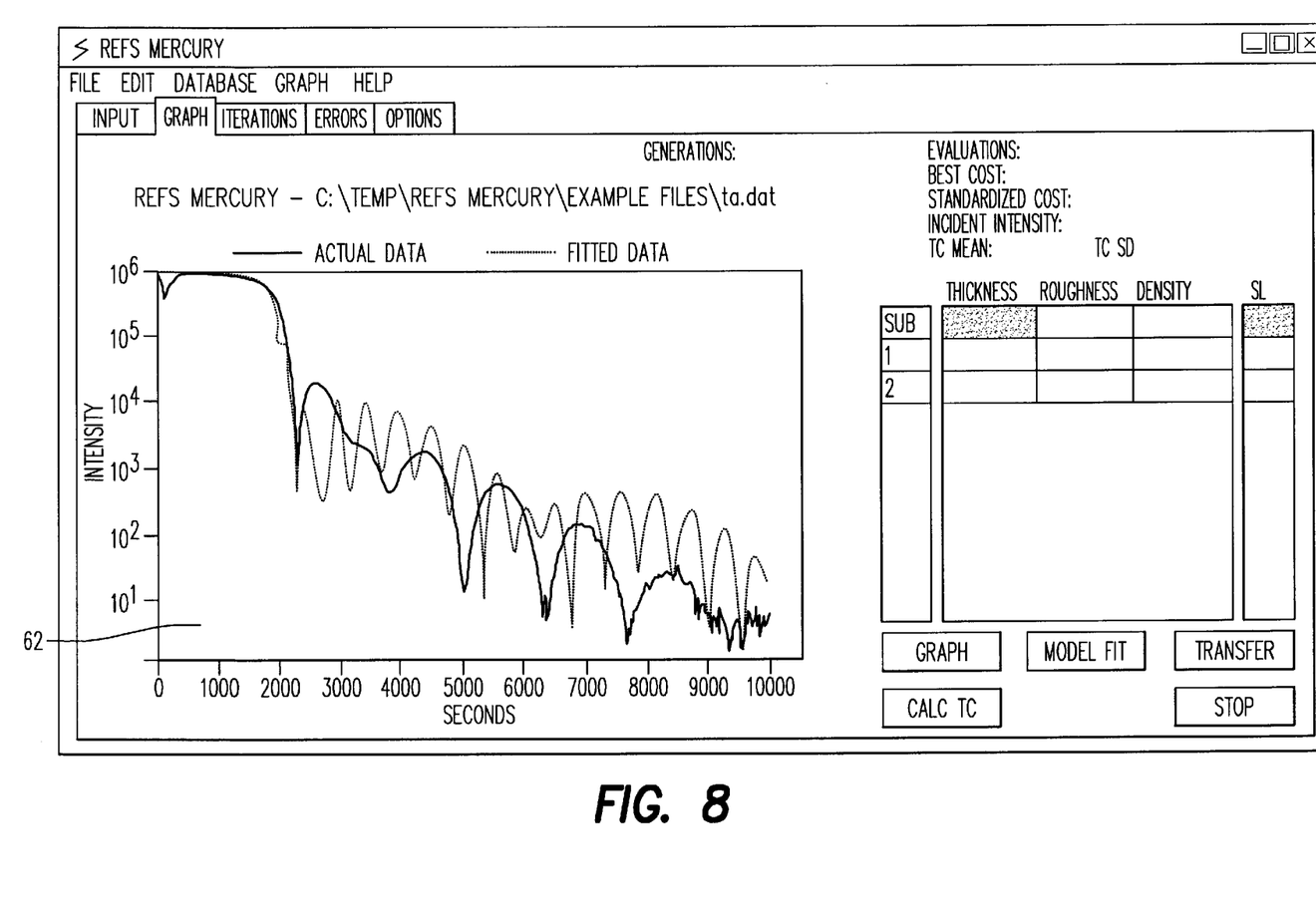
FIG. 8 is an illustration of a graph window in the user interface.

Once the initial parameters have been entered, the X-ray scattering data which corresponds to the estimated structure can be simulated, at step 60 of FIG. 6. The user interface enables the operator to view graphs of simulated data which is based upon the initially entered parameters, and compare them with the actual data obtained from the test results. An example of such an interface is shown in FIG. 8. It can be seen that the graphs depicted in a window 62 of this example are similar to those of FIG. 5a.

Figure 9:
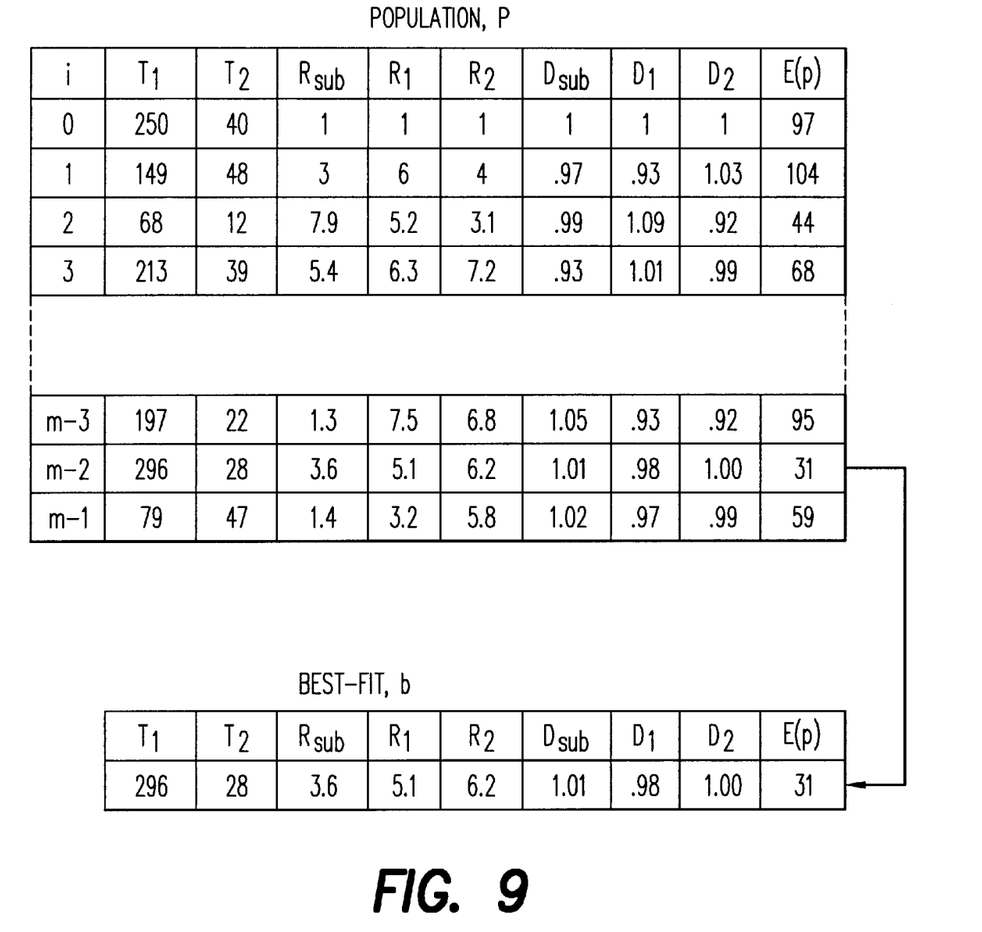
FIG. 9 is a chart representing an exemplary initial population in the application of an evolutionary algorithm to X-ray scattering data.

The original parameter values entered by the user can be employed to generate an initial population of parameter vectors which described other estimated models to be evaluated against the measured data. The parameters for estimated models can be stored in an array which holds a population of m, n-dimensional real valued parameter vectors P=[(p$_0$, p$_1$p$_2$..., p$_{m-1}$]. In the example of FIG. 7, therefore, n=8. The value for n is arbitrary, and might be 10×x n, for example. The parameter vector po is initialized from the user's original guess at the structure, i.e., the values entered in the user interface. The remaining m−1 vectors are initialized at step 64 (FIG. 6) by assigning to each parameter a randomly chosen value from within an allowed range. An example of an initial population is depicted in FIG. 9. Referring thereto, the first member of the population, vector P$_o$, has parameter values corresponding to the original values entered by the operator. The other m−1 members of the initial population can be generated in a variety of ways. For example, one approach is to randomly select a number within the range of high and low values entered by the user. Another approach is to randomly mutate the original values entered by the user. For instance, a predetermined number or a randomly generated number can be selectively added to or subtracted from the parameter values entered by the operator, to generate the successive members of the population.

Once the initial population is complete, X-ray scattering data is simulated for the parameters of each parameter vector at step 66, and the error function for each p$_i$ is evaluated, at step 68. The error value E(p) associated with each vector is also shown in the array of FIG. 9. After the initial population of vectors is analyzed, the random recombination and mutation of members of the first population is used to create an offspring population, at step 70. The X-ray scattering data for each member of the offspring population is simulated at step 72, and the fitness of that simulated data is evaluated at step 74, using the error function. Thereafter, at step 76, the parent population is updated by selecting those members of the offspring population which provide a better fit to the experimental data. As each new member is added to the parent population, its data curve can be displayed at step 78.

This procedure then continues in an iterative fashion, until a predetermined condition is detected at step 80 (FIG. 6), which causes the process to terminate. At this point, the member of the latest population which has the lowest error value E(p) is selected as the vector with the best fit for the experimental data.

In a preferred embodiment of the present invention, a particular evolutionary algorithm known as differential evolution is employed to find the best fit for the experimental data. For detailed information on differential evolution per se, reference is made to K. Price and R. Storn, "Differential Evolution", *Dr. Dobb's Journal*, April 1997, pp. 18–24 and 78; and R. Storn & K. V. Price, "Differential Evolution—A Simple and Efficient Scheme for Global Optimization Over Continuous Spaces", *Technical Report* TR-95-012, ICSI, URL http://http.icsi.berkely.edu/~storn/litera.htm1, the disclosures of which are incorporated by reference herein. In accordance with the invention, this algorithm is employed to locate the most appropriate model for a set of X-ray scattering test data. A particular advantage of differential evolution is that it provides more flexibility when choosing the error function, since it is only necessary to choose a continuous function, and does not require continuous derivatives.

Figure 10:
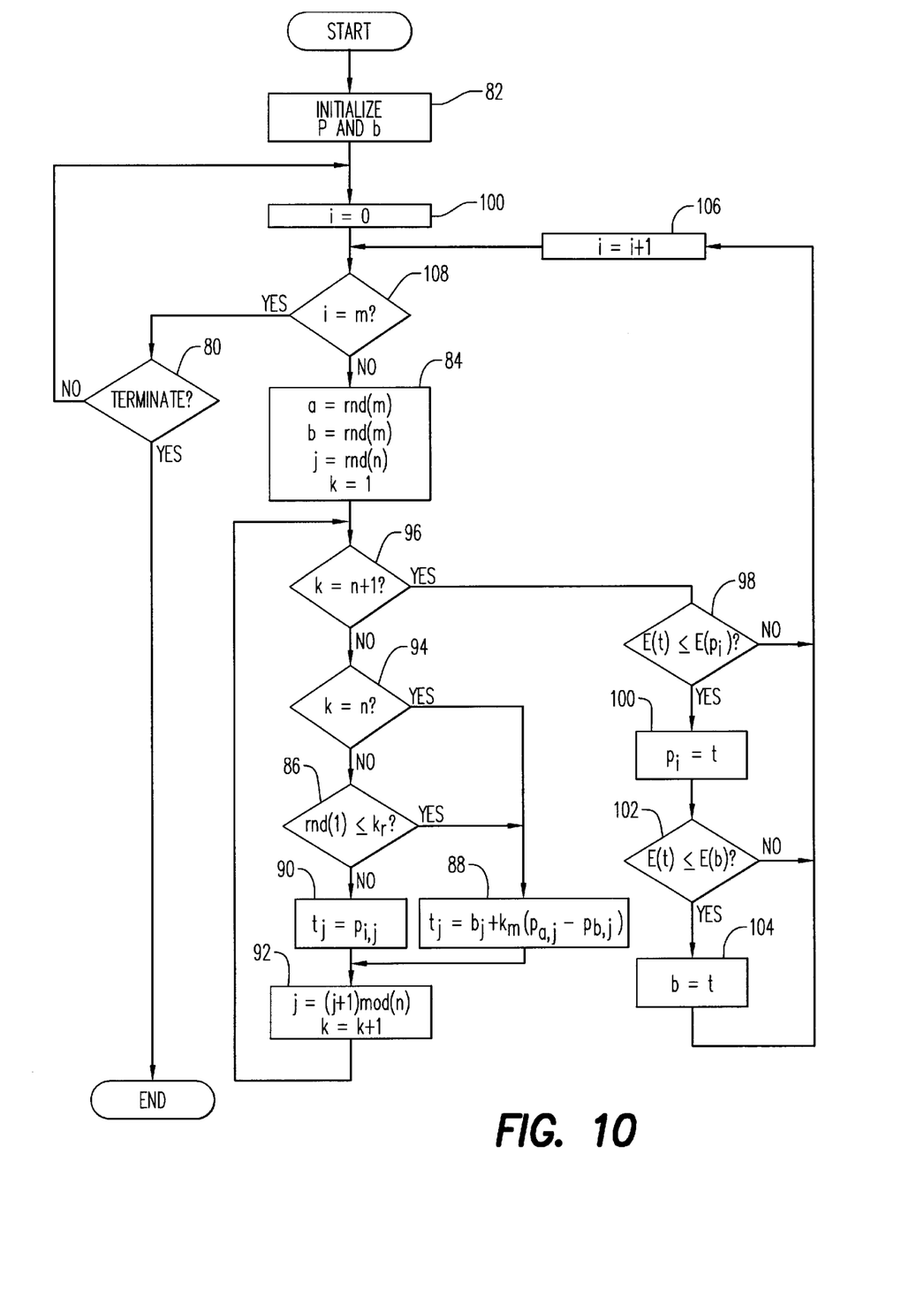
FIG. 10 is a more detailed flowchart of the use of differential evolution to create members of a new population.

A more detailed flowchart which depicts the application of differential evolution to X-ray scattering data is illustrated in FIG. 10. At step 82, the initial population P is generated, as depicted in FIG. 9. In addition, the parameter vector with the lowest error is stored as a vector b=(b$_1$,b$_2$..., b$_n$). This vector is used to track the progress of the optimization process, and is updated whenever an equal or better solution for the best-fit vector is found. In the example of FIG. 9, the parameter vector P$_{m-2}$ is selected as the vector b.

The differential evolution algorithm employs a relatively simple approach to create new population members. Two randomly selected vectors, P$_a$ and P$_b$' are chosen from the current population. Their difference is then used to mutate the best-fit vector, b, according to the relation $$b'=b+k_m(p_a-p_b) \quad (5)$$

where k$_m$ is a mutation constant. The value of k$_m$ is empirically selected to provide fast convergence. In an exemplary embodiment of the invention, k$_m$=0.7. As population vectors converge during the process, the differences between them diminish and the difference vector, (p$_a$−p$_b$), remains scaled to a size appropriate for the evolving population.

Once the vector b' is computed, a trial vector, t=(t$_1$,t$_2$, ..., t$_n$), is assembled which competes with the parameter vectors p$_0$ for membership in the next generation of the population. Starting with a randomly chosen parameter j at step 84, the trial parameters t$_j$ are randomly loaded consecutively, modulo n, from either b' or from p$_0$. A binomial distribution can be employed to decide which trial vector parameters will be contributed by b' and which will come from p$_0$. A random number in the uniform range (0,1) is chosen and compared to a user-selected recombination constant k$_r$ at step 86. If the random number is less than or equal to k$_r$, then t$_j$ is loaded with the j-th parameter from b', at step 88. If the random number is greater than k$_r$, the j-the parameter comes from p$_0$ at step 90. The value for is incremented at step 92, and steps 86–90 are repeated for each parameter. At the nth trial, t gets its final parameter from b', via step 94, to ensure that at least one parameter value of t is different from p$_0$. Once the vector t is assembled in this manner, applicable constraints are taken into account. If the value of a trial parameter t$_j$ falls outside of the user-specified limits, it is replaced by a randomly selected value according to the expression:

$$t_j = p_j^{min} + \text{rand}(p_j^{max} - p_j^{min})$$

where p$_j^{min}$ and p$_j^{max}$ denote the minimum and maximum permissible values for the j-the parameter, respectively.

Thereafter at step 96, the new trial vector t is tested against p$_0$ as a candidate for the next generation. The new trial vector is only selected to replace $p_0$ in the next generation if it satisfies the inequality $$E(t) \leq E(p_0). \quad (6)$$

If this condition is satisfied at step 98, $p_0$ is replaced with t at step 100. Otherwise, $p_0$ propagates to the next generation.

If t becomes the newest member of the population, it is compared to the best-fit vector b at step 102, to see if its error value is less than that of b. If so, t replaces b as the best-fit vector, at step 104.

Thereafter, the index i is incremented at step 106, and the other members $p_i$ of the prior generation are successively evaluated against the error function to fully populate the new generation. A newly mutated vector b' is calculated each time, through the random selection of the parameter vectors $p_a$ and $p_b$ at step 84. Each of the members of the new generation represents the better fit between a trial vector and the corresponding member of the prior generation. The second generation has been fully populated once the index i is equal to m, as detected at step 108. At this point, a determination is made at step 80 whether to terminate the process. If it is not to be terminated, the procedure returns to step 100, to populate the next generation of parameter vectors.

Figure 11:
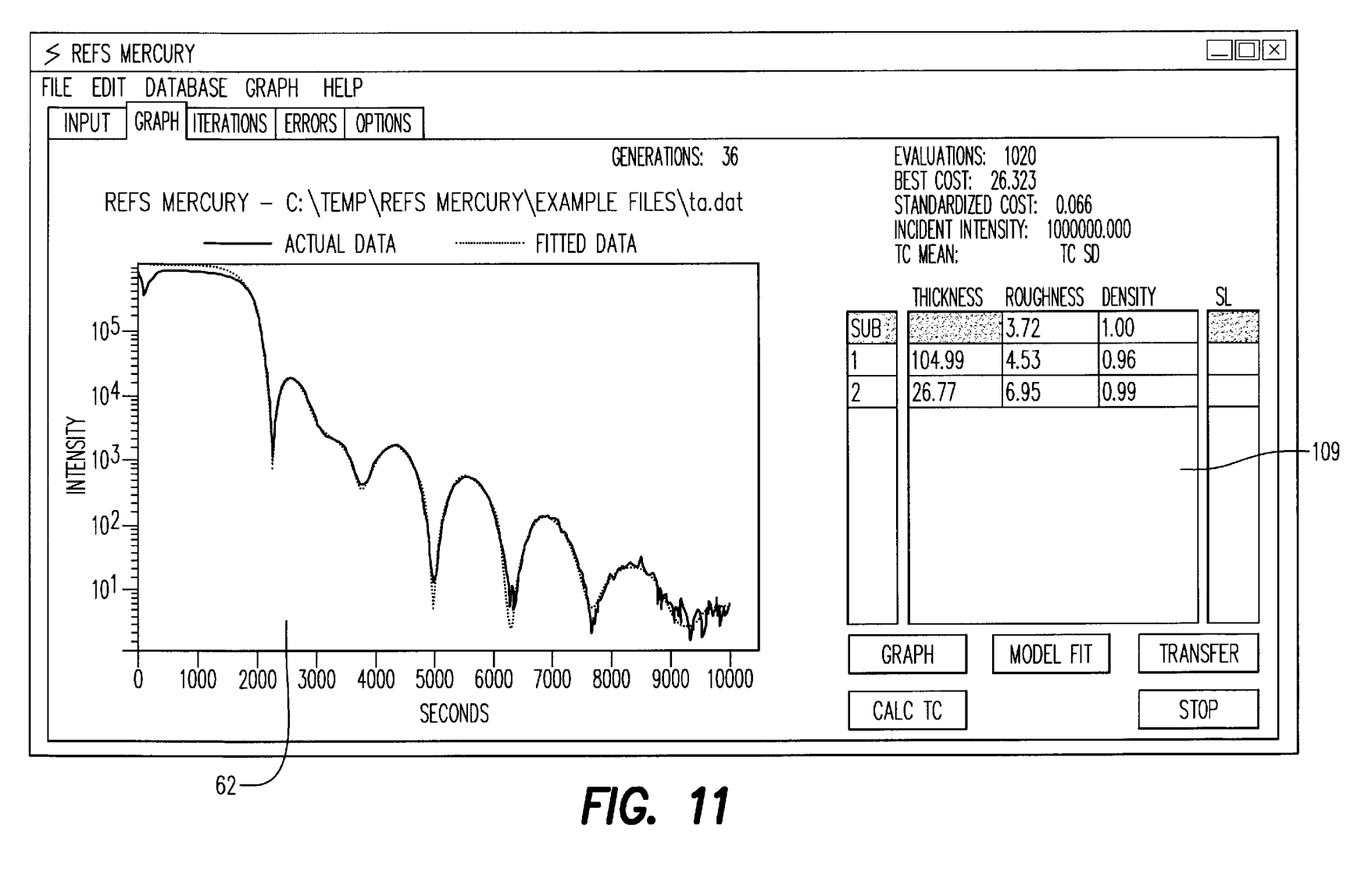
FIG. 11 is an illustration of a final results window that is displayed after the fitting process as terminated.

FIG. 11 illustrates the results that were obtained for the example of FIG. 7 after 36 generations of vectors have been evaluated. These results were obtained over the course of only a few minutes, even though the original estimate was far from the best-fit values. As can be seen, the simulated data for the final selection closely matches the actual data. The parameters associated with this final selection are displayed in a results window 109.

The decision to terminate the process at step 80 could be responsive to a variety of different factors. For instance, it could be as simple as manual intervention by the operator issuing a command to stop. Alternatively, the operator may have set a maximum number of iterations to be carried out. Preferably, however, the process continues until the simulated data converges to the best possible fit. In accordance with this feature of the invention, a determination is made of the theoretically best error value that can be obtained for a set of data, and the evolutionary process is terminated when the simulated data lies within a certain range of this best theoretical value.

Physically, the error function should indicate how close the simulated model is to the actual specimen. It provides a number that represents the "closeness" of two data sets. The objective, therefore, is to determine whether it is possible to predict a minimum error value $E_{min}$ for a given (noisy) data set, and a perfect model.

A significant consideration in the ability to make such a prediction is the fact that simulation of X-ray scattering data is an extremely accurate process. Moreover, the noise distributions on X-ray generation and detection are accurately represented by a Poisson distribution. Ideally, therefore, barring errors in computation, $E(p)=0$. In other words, the experimental and simulated data are identical, and represented by $I(\theta_j,p)$. Introducing Poisson noise into a perfect simulation creates the following theoretical value at any point:

$$I'(\theta_j,p) = I(\theta_j,p) + \Delta I_j \quad (7)$$

where $\Delta I_j$ is a random deviate selected from a Poisson distribution appropriate for a given incident intensity.

A minimum expected error value $E_{min}$ can be calculated for data acquired in a given time with a given incident intensity when the model is an accurate representation of the sample and when best convergence is reached. The easiest and most reliable way to calculate $E_{min}$ is to run a set of simulations of the data from the converged model, with Poisson noise added as appropriate to the counting statistics. For instance, setting $I_j$ equal to $I'(\theta_j,p)$ in the chosen error function of any of Equations 1–4 provides the error value $E(p)$ that is due to statistical noise in a single realization of $I'(\theta_j,p)$. Running 100 such simulations gives a reliable mean value of $E_{min}$ and of its standard deviation, $\Delta E_{min}$, which indicates the minimum error function than can be expected if the model is good and fully converged in the presence of noisy data. In other words, it is the best error function value that the data can sustain. The actual error function can then be tested for (a) convergence, and (b) absolute comparison with Equation 7 above. It is converged in practice if its value is $$E < E_{min} + 3\Delta E_{min}. \quad (8)$$

If the model data has converged, in the sense that it is not changing any more, but is substantially larger than the theoretical value set forth in Equation 8, this indicates a deficiency in the model. If it satisfies Equation 8, there is no need to test separately for convergence; this is as good a solution as the data can sustain.

The data-fitting method results in best-fit parameter values, which can be reported to as many decimal places as desirable. In the system of the present invention, it is possible to assess the reliability and accuracy of these values. It is difficult to calculate the true error in any parameter with respect to the variation of all other parameters, since it is a state calculation of the model in a significantly large region of parameter space. However, it is feasible to calculate the point-wise parameter uncertainties of each variable, taken around the position determined as the global minimum. This is defined for the parameter $p_j$ as the change in $p_j$ that will produce a defined change in the error function $E(p)$, with all other parameters kept constant. This change can be defined as 5% of the minimized value of $E(p)$, since this change is normally easily recognizable in the simulated data. The change is specifically calculated for both signs of the deviation of $p_j$, since the error function can be asymmetric. It is then easily seen which parameters are well determined by the fitting procedure, and which are poorly determined.

Figure 12:
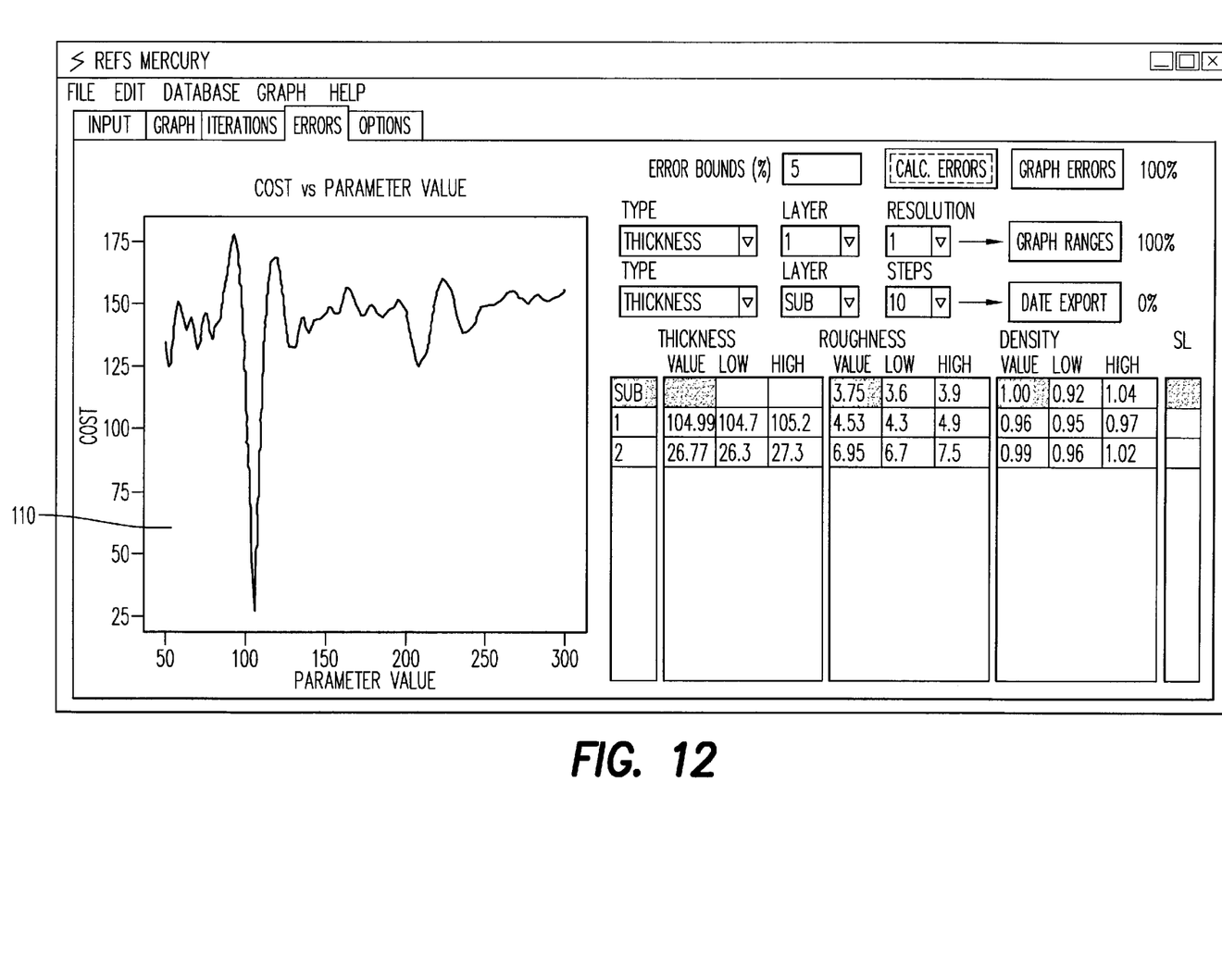
FIG. 12 is an illustration of an error window depicting the uncertainty associated with one of the final parameter values.

FIG. 12 illustrates an example of such a determination for the thickness of layer 1, i.e., the Ta layer 22. As illustrated in FIG. 11, the best fit for this parameter is a value of 104.99. All of the other parameters are fixed at their best-fit values, and the parameter being evaluated is varied over a suitable range. The error value $E(p)$ is calculated as the parameter is varied. A graph of the error value over this range is displayed in a window 110. As can be seen for this particular example, the error value increases rapidly when the parameter is varied from its best-fit value, thereby providing a relatively high level of certainty with regard to the final result. This information can be used to specify tolerances for manufactured components. Since a simulation may also be compared with a noisy simulation (i.e. one with statistical noise included), it is also possible to use this feature to design an experiment that will better determine parameters which are poorly defined. For instance, a large range of uncertainty for a given parameter can indicate that the experimental measurement was insensitive to the value of that parameter.

It is also possible to allow the system to discover new features in the specimen. If, for example, lower density surface layers, e.g., an oxide layer, or interdiffused interface layers are suspected, they can be inserted as additional layers with a range of composition or density (as appropriate) that allows them either to be separate layers or to merge with an adjacent layer. The fitting procedure is then repeated. By comparing the converged error value to $E_{min}$ from Equation 8, and calculating the pointwise parameter errors, the presence of such additional layers can be confirmed or refuted.

From the foregoing, it can be seen that the application of evolutionary algorithms to the fitting of X-ray scattering data provides a quick, yet robust, solution to the problem of characterizing the structure of a specimen from its experimental data. By utilizing both mutation and recombination of existing data, the evolutionary algorithm optimizes the tradeoff between exploring new points in a parameter space and exploiting information that has been previously obtained. In addition, since evolutionary algorithms operate on several solutions simultaneously, information is gathered from current search points to guide the direction of new searching. Thus, the parameter space can be extensively searched without having to test all values. Furthermore, the ability to maintain multiple solutions concurrently reduces the likelihood of settling on a local minimum in the error values. Optimum solutions can be reached in a matter of minutes, rather than hours or days.

It will be appreciated by those of ordinary skill in the art that the present invention can be embodied in other specific forms without departing from the spirit or essential characteristics thereof. For instance, while an exemplary embodiment of the invention has been described with reference to X-ray reflectivity information, the principles of the invention are applicable to all forms of X-ray metrology, where it is desirable to determine the best simulated model for a given set of experimental data. For example, high-resolution X-ray diffraction data can be used in the context of the invention to determine information about parameters such as composition, quality, strain, thickness and tilt of crystalline layers. In general, the techniques of the present invention can be applied to a variety of different types of inverse problems, where physical parameters must be inferred from simulated data models.

Furthermore, while differential evolution has been identified as a particularly appropriate approach to determine the best fitting model, other evolutionary algorithms can be employed as well. Similarly, other error functions can be employed to determine how closely the estimated data fits the measured results.

The presently disclosed embodiments are therefore considered in all respects to be illustrative, and not restrictive. The scope of the invention is indicated by the appended claims, rather than the foregoing description, and all changes that come within the meaning and range of equivalents thereof are intended to be embraced therein.

What is claimed is:

1. A method for estimating parameters of a material, comprising the steps of:

obtaining experimental x-ray scattering data which is indicative of parameter values for the material;

estimating a model for the material and calculating simulated x-ray scattering data for the estimated model;

comparing the experimental and simulated x-ray scattering data to generate an error value;

modifying the model by means of an evolutionary algorithm to reduce said error value; and reporting the parameter values which characterize the modified model as an estimate of the parameter values for the material.

2. The method of claim 1 wherein said evolutionary algorithm is differential evolution.

3. The method of claim 2 wherein said model is modified by computing a plurality of parameter vectors which respectively define different models, generating a test vector which is based, at least in part, upon a difference between parameter vectors, comparing an error value for said test vector with an error value for a designated one of said plurality of parameter vectors, and choosing the vector having the smaller error value as a new estimate for said model.

4. The method of claim 3 wherein said test vector is generated by mutating one of said plurality of parameter vectors in accordance with differences between said two parameter vectors; and randomly selecting individual parameters from either said mutated vector or a given one of said plurality of parameter vectors to form the test vector.

5. The method of claim 4 wherein the given parameter from which the individual parameters are selected is the same as said designated parameter vector against which said test vector is compared.

6. The method of claim 4 wherein the parameter vector which is mutated is the parameter vector having the lowest error value among said plurality of parameter vectors .

7. The method of claim 1 wherein s aid error value is generated by means of a function based on logarithmic values of the scattering data.

8. The method of claim 7 wherein said function is the mean-absolute error of the log-transformed data.

9. The method of claim 1 wherein said error value is generated by means of a function based on absolute differences between the experimental and simulated scattering data.

10. The method of claim 1 further including the steps of determining a theoretical minimum error value for the x-ray scattering data, and repeating said modifying step until the reduced error value converges within a predefined range of said theoretical error value.

11. The method of claim 10 wherein said predefined range is equal to three standard deviations of said theoretical value.

12. The method of claim 1 further including the step of determining the uncertainty of an estimated parameter value by varying one of said estimated parameter values while maintaining the other parameters at their estimated values, and determining the change in the error value associated with said variation.

13. A method for estimating parameters of a material, comprising the steps of:

i) obtaining experimental x-ray scattering data which is indicative of parameter values for the material;

ii) estimating a first vector of parameters for the material;

iii) generating additional parameter vectors from said first vector parameter;

iv) simulating x-ray scattering data for each of said parameter vectors and calculating an error value for each parameter vector based upon a comparison of the experimental and simulated scattering data;

v) generating a test vector which is based upon random mutation of at least one of said parameter vectors;

vi) comparing an error value for said test vector with the error value for a designated one of said parameter vectors; and vii) selecting the vector having the lower error value as a new estimate for the parameters of the material.

14. The method of claim 13 further including the steps of calculating a theoretical minimum error value, and iteratively repeating steps (v)–(vii) until the error value for the selected vector is within a predefined range of said theoretical error value.

15. The method of claim 14 wherein said predefined range is equal to three standard deviations of said theoretical value.

16. The method of claim 13 wherein the test vector is generated by randomly selecting individual parameters from either a mutated parameter vector or said designated parameter vector.

17. The method of claim 13 wherein a parameter vector is mutated by determining a difference between two of said parameter vectors and applying said difference to a third parameter vector.

18. The method of claim 17 wherein said third parameter vector is the parameter vector having the lowest error value among said plurality of parameter vectors.

19. The method of claim 13 wherein said error value is generated by means of a function based on logarithmic values of the scattering data.

20. The method of claim 19 wherein said function is mean-absolute error of the log-transformed data.

21. The method of claim 13 wherein said error value is generated by means of a function based on absolute differences between the experimental and simulated scattering data.

22. The method of claim 13 further including the step of determining the uncertainty of an estimated parameter value by varying one of said estimated parameter values while maintaining the other parameters at their estimated values, and determining the change in the error value associated with said variation.

23. A computer-readable medium containing a program which executes the steps of:

calculating simulated x-ray scattering data for an estimated model of a material;

comparing the simulated x-ray scattering data with experimental data to generate an error value;

modifying the model by means of an evolutionary algorithm to reduce said error value; and reporting the parameter values which characterize the modified model as an estimate of the parameter values for the material.

24. A computer readable medium containing a program which executes the steps of:

generating a plurality of parameter vectors for a material;

simulating x-ray scattering data for each of said parameter vectors and calculating an error value for each parameter vector based upon a comparison of experimental data and said simulated scattering data;

generating a test vector which is based upon random mutation of at least one of said parameter vectors;

comparing an error value for said test vector with the error value for a designated one of said parameter vectors; and selecting the vector having the lower error value as a new estimate for the parameters of the material.

\* \* \* \* \*